United States Patent
Obata et al.

(10) Patent No.: US 7,206,378 B2
(45) Date of Patent: Apr. 17, 2007

(54) X-RAY ANALYSIS APPARATUS

(75) Inventors: Yasushi Obata, Hanno (JP); Kohji Kakefuda, Akishima (JP)

(73) Assignee: Rigaku Corporation, Akishima-Shi, Tokyo (JP)

( * ) Notice: Subject to any disclaimer, the term of this patent is extended or adjusted under 35 U.S.C. 154(b) by 0 days.

(21) Appl. No.: 11/066,142

(22) Filed: Feb. 25, 2005

(65) Prior Publication Data

US 2005/0190881 A1  Sep. 1, 2005

(30) Foreign Application Priority Data

Feb. 27, 2004  (JP)  ............................. 2004-054521

(51) Int. Cl.
*G01N 23/20* (2006.01)
*H04G 1/28* (2006.01)

(52) U.S. Cl. ............................ 378/71; 378/70; 378/162

(58) Field of Classification Search ............ 378/70–90, 378/162; 345/440
See application file for complete search history.

(56) References Cited

U.S. PATENT DOCUMENTS

2005/0099423 A1 * 5/2005 Brauss ....................... 345/440
2006/0078195 A1 * 4/2006 Vaillant et al. ............. 382/154

FOREIGN PATENT DOCUMENTS

| JP | 55-110940 | 8/1980 |
|---|---|---|
| JP | 1-114741 | 5/1989 |
| JP | 2-266249 | 10/1990 |
| JP | 4-225152 | 8/1992 |
| JP | 2000-258366 | 9/2000 |
| JP | 2004-28686 | 1/2004 |

* cited by examiner

*Primary Examiner*—Edward J. Glick
*Assistant Examiner*—Irakli Kiknadze
(74) *Attorney, Agent, or Firm*—Buchanan Ingersoll & Rooney PC (57) ABSTRACT

An X-ray analysis apparatus includes: an X-ray radiation unit that irradiates a sample with X-ray; an X-ray detection unit that detects X-ray emission from the sample; a unit that allows the X-ray detection unit to perform scanning operation for changing the angle of the X-ray detection unit with respect to the sample; and an image controller that displays information related to X-ray intensity detected by the X-ray detection unit and information related to a scanning angle of the X-ray detection unit as a 3D image. The image controller displays the 3D image simultaneously with the scanning operation of the X-ray detection unit. Further, simultaneously with the scanning operation of the X-ray detection unit, two or all of 1D, 2D, and 3D images are displayed in one screen. A measurement result starts being displayed as a 3D image before information related to all measurement results has been obtained.

12 Claims, 8 Drawing Sheets

A ⟶ (2θ SCANNING DIRECTION)

Fig. 7B

A ⟶ (2θ SCANNING DIRECTION)

Fig. 8A

A ⟶ (2θ SCANNING DIRECTION)

Fig. 8B

A ⟶ (2θ SCANNING DIRECTION)

X-RAY ANALYSIS APPARATUS

BACKGROUND OF THE INVENTION

1. Field of the Invention

The present invention relates to an X-ray analysis apparatus that analyzes a sample using X-ray.

2. Description of the Related Art

At present, various X-ray analysis apparatuses such as an X-ray diffractometer, an X-ray small angle measurement apparatus, and a fluorescent X-ray analysis apparatus are known. The above X-ray analysis apparatuses irradiate a sample with X-ray and detect X-ray radiation (diffracted radiation, scattered radiation, fluorescent X-ray, or the like) from the sample using an X-ray detector. More specifically, the central line of X-ray incident on the sample, or so-called incident X-ray optical axis is set at 0°. The analyzers then detect the angle of the X-ray radiation with respect to the incident X-ray optical axis and the intensity of the radiation, thereby determining physicality of the sample.

To observe the angle of the X-ray radiation with respect to the incident X-ray optical axis and the intensity of the radiation, the results of the above measurement are represented by a graph obtained by plotting X-ray radiation angle "$2\theta$" and X-ray radiation intensity "I" on a coordinate system with angular positions of X-ray emitted from the sample on the horizontal axis and intensities of X-ray on the vertical axis. The graphic form obtained in the graph is referred to as X-ray diffraction diagram or the like. Further, known is an X-ray analysis apparatus configured to display the above-mentioned graph on an electrical display unit, such as a CRT (Cathode Ray Tube) display, an LCD (liquid crystal display), which is disclosed, for example, in Japanese Patent Laid-Open Publication No. 2000-258366. The conventional X-ray analysis apparatus firstly obtains all data items related to the X-ray intensity, and then displays the X-ray diffraction diagram on the display unit.

In general, the X-ray measurement performed by the X-ray analysis apparatus is time consuming. It takes several hours or several tens of hours to end the measurement. In some cases, the measurement is performed for several days. The X-ray measurement is not always performed under the optimal condition. For example, there is a case where a sample to be used differs from expected one, or measurement condition is not compatible with the sample. In such a case, conventionally, whether the sample itself or measurement condition has been adequate or not is determined by the measurement result. Therefore, the determination is not made until the measurement result has been displayed after the completion of the measurement. Thus, in the case where the sample itself or measurement condition is not adequate, the time engaged in the measurement comes to nothing.

SUMMARY OF THE INVENTION

The present invention has been made to solve the above problem, and an object thereof is to provide an X-ray analysis apparatus capable of quickly and accurately perform an X-ray measurement in the case where the measurement is carried out by allowing an X-ray detecting means to perform scanning operation.

According to an aspect of the present invention, there is provided an X-ray analysis apparatus including: an X-ray radiation means for irradiating a sample with X-ray; an X-ray detecting means for detecting X-ray emission from the sample; a means for allowing the X-ray detecting means to perform scanning operation for changing the angle of the X-ray detecting means with respect to the sample; and an image control means for displaying information related to X-ray intensity detected by the X-ray detecting means and information related to a scanning angle of the X-ray detecting means as a 3D image, wherein the image control means displays the 3D image simultaneously with the scanning operation of the X-ray detecting means.

The operation flow of the conventional X-ray analysis apparatus is that all information related to measurement is firstly obtained, then the obtained measurement information is subjected to image processing, and a measurement result is displayed on the display unit as an X-ray diffraction diagram. In the X-ray analysis apparatus according to the present invention, on the other hand, a measurement result starts being displayed, as a 3D image, simultaneously with scanning operation of the X-ray detecting means, that is, before all measurement information have been obtained. Therefore, it is possible to check a part of the measurement information displayed in a 3D manner, that is, the measurement information within a short span of time after the start of the measurement, which enables an operator to accurately determine whether the used sample is adequate or not, or whether measurement condition is adequate or not.

Further, in the present invention, angular information and intensity information related to X-ray is displayed as a 3D image. The operator can therefore obtain more various kinds of information compared to the case where the information is displayed in a 1D or 2D manner. That is, according to the present invention, it is possible to perform X-ray measurement quickly and accurately.

Three types are available as the X-ray detecting means in view of the way of capturing X-ray: a 0-dimensional X-ray detecting means, a one-dimensional X-ray detecting means, and a two-dimensional X-ray detecting means. The 0-dimensional X-ray detecting means captures X-ray in a dotted manner. Examples of this type include a PC (Proportional Counter), a SC (Scintillation Counter) and the like.

The one-dimensional X-ray detecting means captures X-ray as a line. Examples of this type include a PSPC (Position Sensitive Proportional Counter), a one-dimensional CCD (Charge Coupled Device) X-ray detector formed by configuring a plurality of CCDs as a line, and the like. The two-dimensional X-ray detecting means captures X-ray as a plane. Examples of this type include an X-ray film, a planar storage phosphor film in which a storage phosphor is formed on an X-ray receiving surface as a film, a two-dimensional CCD X-ray detector formed by configuring a plurality of CCDs as a plane.

The one-dimensional X-ray detecting means can capture X-ray as a line. The two-dimensional X-ray detecting means also can capture X-ray as a line. It is preferable that the X-ray detecting means be capable of capturing X-ray as a line as described above in the X-ray analysis apparatus according to the present invention. In particular, it is preferable that a linear X-ray capture region of the X-ray detecting means be formed so as to extend in the direction perpendicular to the scanning direction of the X-ray detecting means.

Thus, when the scanning operation of the X-ray detecting means is performed, X-ray information related to a certain region in the perpendicular direction to the scanning direction can be simultaneously obtained. The operator can therefore obtain more various kinds of X-ray information compared to the case where the 0-dimensional X-ray detecting means is used.

A term "perpendicular" here may be strict or approximate as far as the X-ray detecting means can capture a perpendicular component of X-ray information with respect to the scanning direction.

According to anther aspect of the present invention, there is provided a second X-ray analysis apparatus including: an X-ray radiation means for irradiating a sample with X-ray; an X-ray detecting means for detecting X-ray emission from the sample; a means for allowing the X-ray detecting means to perform scanning operation for changing the angle of the X-ray detecting means with respect to the sample; and an image control means for displaying information related to X-ray intensity detected by the X-ray detecting means and information related to a scanning angle of the X-ray detecting means simultaneously with the scanning operation of the X-ray detecting means using at least either two image modes selected from three image modes of one-dimensional image, two-dimensional image, and three-dimensional image.

"One-dimensional image (namely, 1D image)" is an image that represents information using lines plotted in the flat. "Two-dimensional image (namely, 2D image)" is an image that represents information using planes plotted in the flat. "Three-dimensional image (namely, 3D image)" is an image that represents information using a perspective expression plotted in the flat.

In the second X-ray analysis apparatus having the above configuration, a measurement result is displayed simultaneously with the scanning operation of the X-ray detecting means, not after the completion of the measurement. Therefore, the operator can determine whether the used sample is adequate or not, or whether measurement condition is adequate or not within a short span of time after the start of the measurement.

Further, at least two of the 1D, 2D, and 3D images are displayed in one screen, so that the operator can observe the measurement result from different viewpoints. Therefore, the operator can make a determination quickly and accurately.

It is preferable that the X-ray detecting means be capable of capturing X-ray as a line in the second X-ray analysis apparatus according to the present invention. That is, it is preferable to use, for example, the one-dimensional or two-dimensional X-ray detecting means. In particular, it is preferable that a linear X-ray capture region of the X-ray detecting means be formed so as to extend in the direction perpendicular to the scanning direction of the X-ray detecting means.

Thus, when the scanning operation of the X-ray detecting means is performed, X-ray information related to a certain region in the perpendicular direction to the scanning direction can be simultaneously obtained. The perpendicular component of the X-ray information cannot be displayed by the 1D image, but can be displayed by the 2D image. However, the 2D image can display the difference in the perpendicular direction only by difference in color or shading. On the other hand, the 3D image can represent the perpendicular component of the X-ray information in a perspective manner, that is, in a spatial manner, so that the operator can make an accurate determination.

DETAILED DESCRIPTION OF THE PREFERRED EMBODIMENTS

An embodiment of the present invention will be described below. In this embodiment, the present invention is applied to an X-ray diffractometer using a θ-2θ system goniometer. It goes without saying that the present invention is not limited to the following embodiment.

Figure 1:
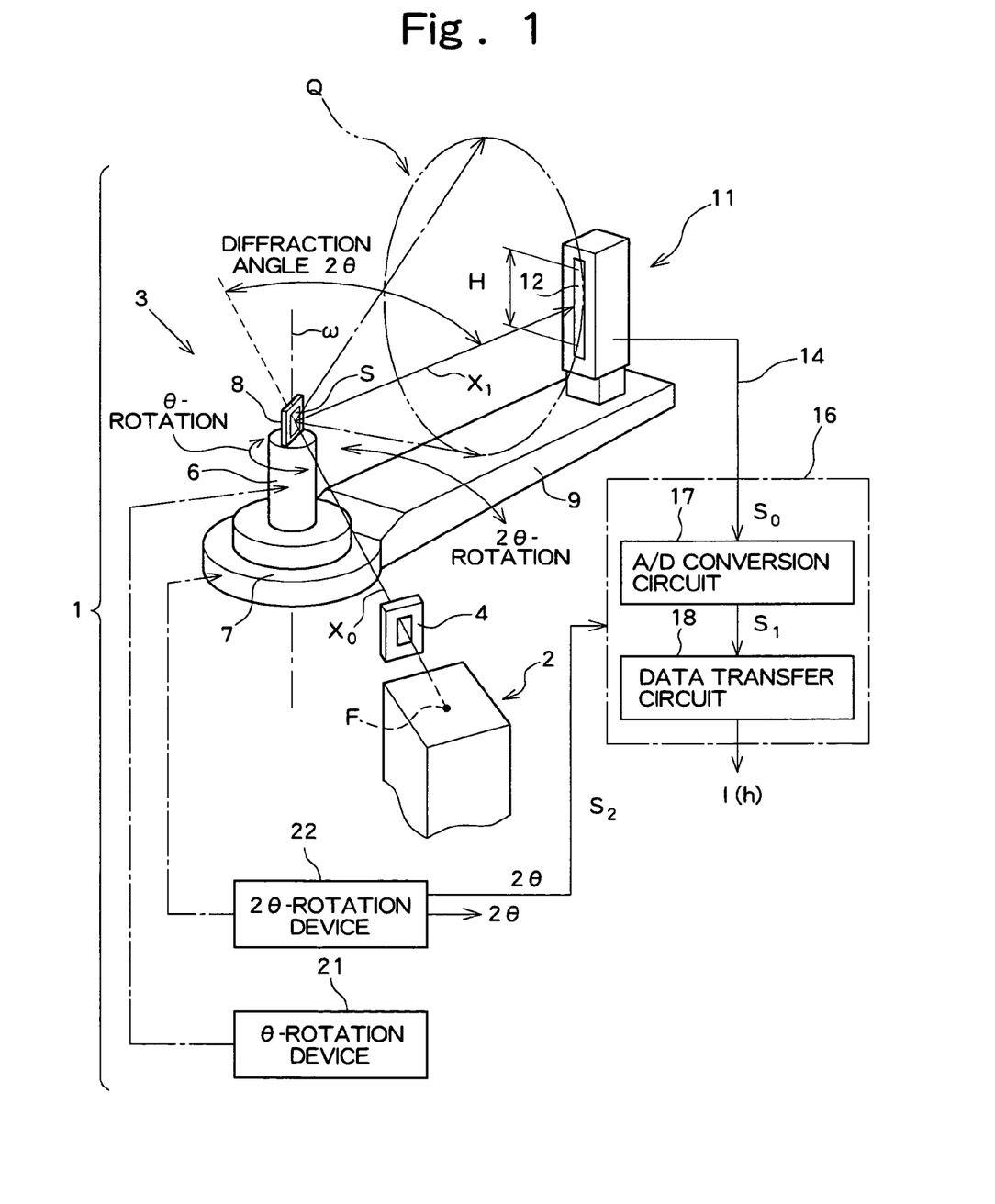
FIG. 1 is a view showing an embodiment of an X-ray analysis apparatus according to the present invention.

FIG. 1 shows a mechanical configuration of an X-ray diffractometer according to the embodiment of the present invention. An X-ray diffractometer 1 shown in FIG. 1 includes an X-ray generator 2 and a goniometer 3, that is, an angle-measuring device. The X-ray generator 2 has an X-ray source "F".

A divergence-limiting slit 4 is provided between the X-ray generator 2 and the goniometer 3. The slit 4 controls the divergence of X-ray so that the X-ray is focused on a sample "S". The goniometer 3 has a θ-rotation table 6 and a 2θ-rotation table 7 situated under the θ-rotation table 6. The θ-rotation table 6 and 2θ-rotation table 7 has the same rotation axis. A sample holder 8 is fitted to the upper surface of the θ-rotation table 6. The sample "S" to be measured is attached to the sample holder 8.

A detector arm 9 extends from the 2θ-rotation table 7 in the direction away from the 2θ-rotation table 7. A CCD detector 11 serving as an X-ray detecting means is secured to the distal end portion of the detector arm 9. The CCD detector 11 is an X-ray detector configured to capture X-ray in a linear capture region, that is, a kind of a 1D X-ray detector. The CCD detector 11 has a linear opening 12 for capturing X-ray as a line.

A θ-rotating device 21 is connected to the θ-rotation table 6. A 2θ-rotating device 22 is connected to the 2θ-rotation table 7. Each of the rotating devices 21 and 22 can be constituted by, for example, a structure that uses an electric motor as a power source and transmits its rotation to the rotation table by a rotation transmission mechanism. As the rotation transmission mechanism, it is possible to adopt, for example, a rotation transmission mechanism constituted by a worm and a worm wheel.

The θ-rotation table 6 is driven by the θ-rotating device 21 to rotate around ω-axis, which passes through the sample "S" attached to the sample holder 8. When the θ-rotation table 6 rotates around ω-axis, the sample "S" on the θ-rotation table 6 also rotates around ω-axis. The rotation of the sample "S" is referred to as θ-rotation, in general.

The 2θ-rotation table 7 is driven by the 2θ-rotating device 22 to rotate around ω-axis. At this time, the detector arm 9 extending from the 2θ-rotation table 7 rotates with the 2θ-rotation table 7, causing the CCD detector 11 secured to the detector arm 9 to rotate around ω-axis. The rotation of the CCD detector 11 is referred to as 2θ-rotation, in general. The direction of the 2θ-rotation is the same as that of the θ-rotation. The speed of the 2θ rotation is double that of the θ-rotation.

The 2θ-rotation has two scanning modes, one of which is a continuous scan and the other of which is a step scan. The continuous scan is a scanning mode that samples the intensity of X-ray by detecting signals at each angle in a specified measurement step while continuously driving the 2θ-rotation table 7. This method can perform the measurement at high speed. The step scan is a scanning mode that repeats a sequence of operations of shifting the 2θ-rotation table 7 by a measurement step angle, stopping it, and counting the intensity of X-ray during the stop time. In the present embodiment, the continuous scan mode that can perform the measurement at high speed is adopted.

When the continuous scan mode is applied to the 2θ-rotation table 7, a 2θ signal output from the 2θ-rotating device 22 is sent, as an exterior trigger signal S2, to an X-ray intensity calculation circuit 16. The timings at which the CCD detector 11 performs the sampling of the X-ray intensity and 2θ angular positions are then synchronized with each other.

The centerline of X-ray that is emitted from the X-ray source "F" and incident on the sample "S" is an optical axis X0 of the incident X-ray. The angle 2θ between the extension line of the optical axis X0 and X-ray emitted from the sample "S" (meaning, in the case of the present embodiment, diffracted X-ray X1 obtained when X-ray incident on the sample "S") is the diffraction angle. The diffracted X-ray that has been diffracted at an angle of 2θ is received and counted by the 2θ-rotating CCD detector 11 when the detector 11 comes to the on the rotating axis of the 2θ-rotation table 7 and thereby know the rotation angular position 2θ of the CCD detector 11 by an output signal from the encoder.

The opening 12 for capturing X-ray that is formed on the CCD detector 11 linearly extends in the direction perpendicular to the 2θ-rotation direction. It is not necessary for the extending direction of the opening 12 is strictly perpendicular to the 2θ-rotation direction. The extending direction of the opening 12 may be tilted slightly with respect to the 2θ-rotation direction. The region of X-ray in the vertical direction within which the CCD detector 11 can capture X-ray depends on a height "H" of the opening 12. The CCD detector 11 has a linear CCD light-receiving surface disposed substantially in parallel with the opening 12, and output terminals thereof are connected to the X-ray intensity calculation circuit 16 through a signal line 14. The X-ray intensity calculation circuit 16 has, for example, an A/D conversion circuit 17 and a data transfer circuit 18.

When X-ray enters in the CCD detector 11 through a certain position in the height "H" of the opening 12, a CCD pixel of the CCD detector 11 which is positioned corresponding to the X-ray incident position in the height "H" outputs a signal S0. The A/D conversion circuit 17 then converts the signal S0 into a count value signal S1. The count value signal S1 is transferred, as an X-ray intensity signal I(h), by the data transfer circuit 18.

Figure 2:
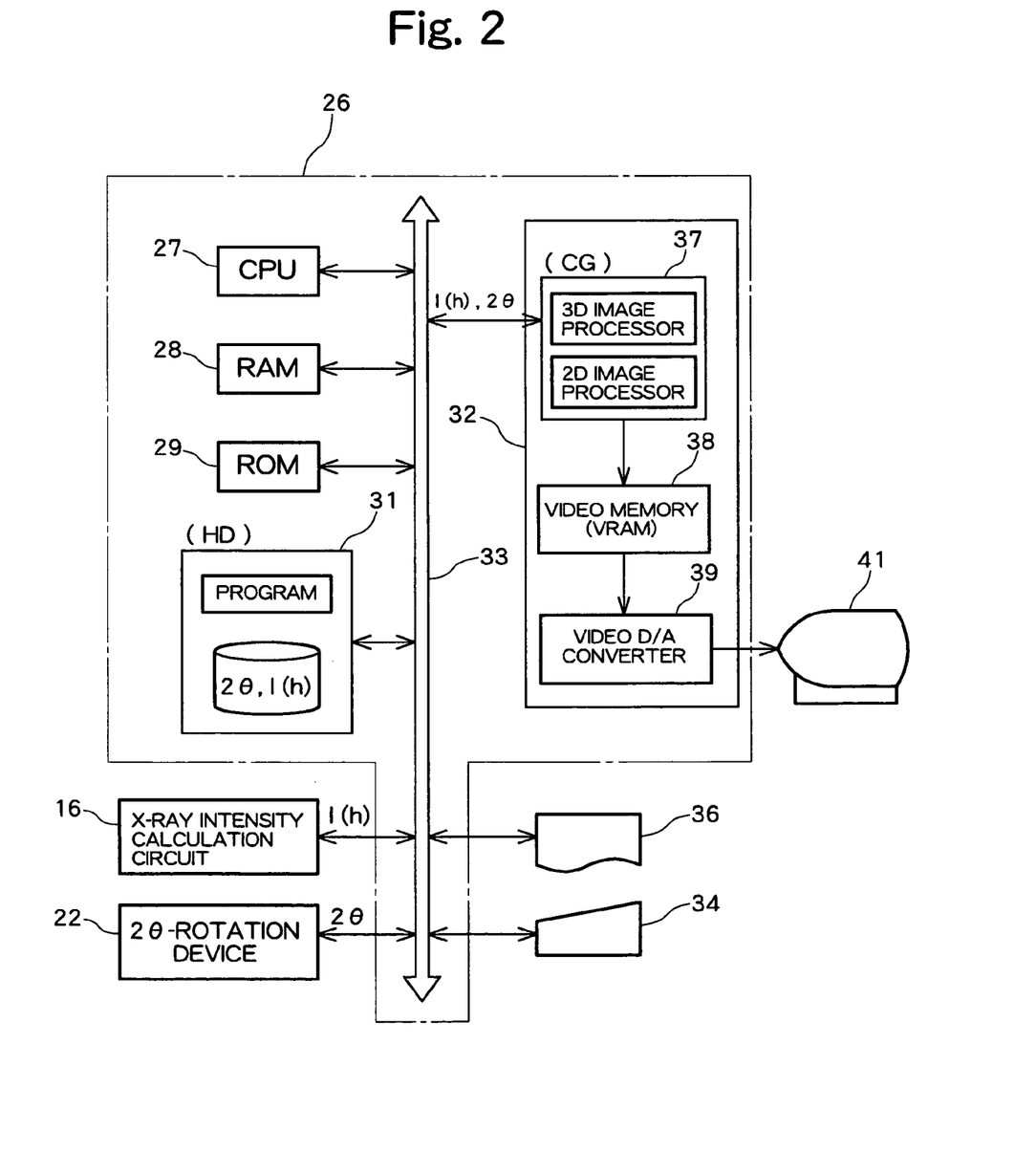
FIG. 2 is a block diagram showing an embodiment of the electrical control system of the analyzer shown in FIG. 1.

FIG. 2 shows the electrical configuration of the X-ray analysis apparatus of FIG. 1. In FIG. 2, the X-ray intensity signal I(h) that has been output from the X-ray intensity calculation circuit 16 of FIG. 1 is input to a processing circuit 26. Further, a diffraction angular signal 2θ that has been output from the 2θ-rotating device 22 of FIG. 1 is input to the processing circuit 26. The processing circuit 26 has a CPU (Central Processing Unit) 27, an RAM (Random Access Memory) 28, an ROM (Read Only Memory) 29, an exterior storage medium 31, an image controller 32, and a bus 33 to which the above components are connected.

In the present embodiment, the X-ray intensity calculation circuit 16 receives the 2θ signal from the 2θ-rotating device 22 as the exterior trigger signal S2 for sampling data. Therefore, the timings at which the X-ray intensity calculation circuit 16 performs the sampling of the X-ray intensity are synchronized with 2θ angular positions. Thus, if the output order of the X-ray intensity signal I(h) which is sequentially output from the X-ray intensity calculation circuit 16 can be identified, it is possible to know the 2θ angle from the order. Therefore, in the case where the X-ray intensity signal I(h) and angle 2θ are related to each other by this method, it is not always necessary for the processing circuit 26 to receive the input of the 2θ signal output from the 2θ-rotating device 22.

The exterior storage medium 31 is constituted by, for example, a hard disk, an MO disk (Magneto Optical Disk), or the like. The exterior storage medium 31 stores a program for controlling the general operation related to the X-ray analysis, a file for storing measurement data of the deffraction angle 2θ, a file for storing measurement data of the X-ray intensity I(h), or the like.

Connected to the bus 33 are an input device 34 such as a keyboard or mouse, and a printing device 36 such as a printer. The image controller 32 has a graphic controller 37, a video memory 38, and a D/A converter 39. The graphic controller 37 has a 2D image processor for creating 1D and 2D images, and a 3D image processor for creating a 3D image. Connected to the output terminal of the D/A converter 39 is an image display unit 41 such as a CRT display or flat display. The graphic controller 37 may be constituted by a dedicated circuit or may be constituted by a part of the program stored in the storage medium 31 in a software-like manner.

An operation of the X-ray analysis apparatus having the above configuration will be described below.

A sample to be measured, for example, a powder sample is attached to predetermined position of the sample holder 8 and the sample holder 8 is fitted to a predetermined position of the Θ-rotation table 6. After necessary measurement conditions, such as a desired measurement range, are input through the input device 34 of FIG. 2, an instruction to start the measurement is issued. As the measurement range, a scanning range with a diffraction angle of, for example, 0° to 100° is designated.

When the instruction to start the measurement has been issued, the 2θ-rotation table 7 rotates to set the CCD detector 11 at an angular position of 0°, which is the initial position of the scanning region. After that, X-ray is emitted from the X-ray source "F" and the sample "S" is irradiated with the X-ray. The sample "S" rotates in a manner of a θ-rotation at a predetermined step angle. At the same time, the CCD detector 11 rotates in a manner of a 2θ-rotation at an angular speed double that of the θ-rotation in the same direction.

When Bragg's condition of diffraction is satisfied between X-ray incident on the sample "S" and the sample "S" during the θ-rotation of the sample "S", X-ray is diffracted by the sample "S". This diffracted X-ray travels while extending in a cone shape, in general. A ring portion "Q", which is a bottom of the cone shape, is referred to as "Debye ring".

When an X-ray film is exposed by the Debye ring "Q", diffraction profiles as shown in FIGS. 7A, 7B, 8A and 8B can be obtained.

In each of these drawings, respective rings are the portions that have been exposed by the Debye ring "Q", and a center point is the position of 2θ=0°. The further from the center point in the radial direction, the larger the diffraction angle 2θ. The scanning direction of the CCD detector 11 of FIG. 1 is is denoted by the arrow "A". The portion that the CCD detector 11 can read is denoted by the rectangle having a height "H".

Figure 7A:
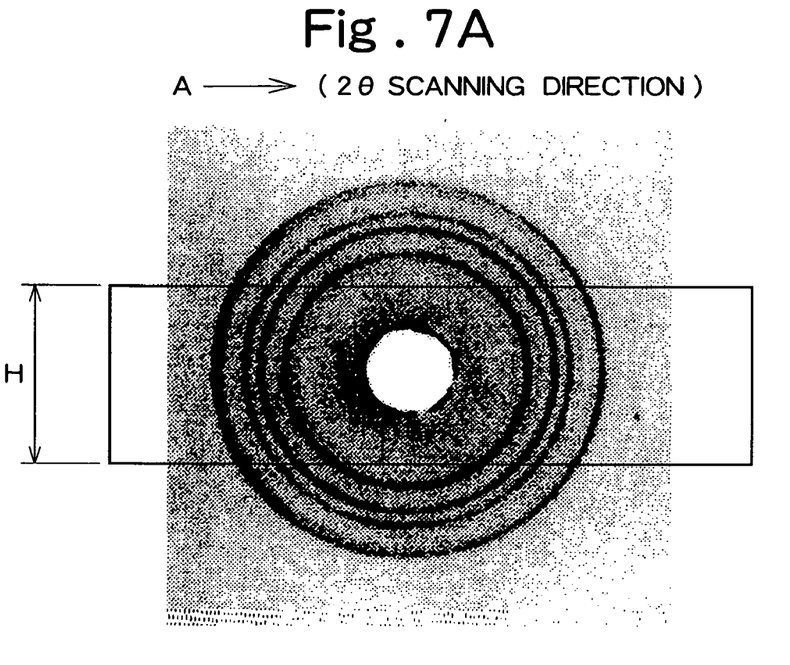
FIGS. 7A and 7B are views, each showing an example of the Debye ring obtained as a result of the measurement using the X-ray analysis apparatus.
Figure 7B:
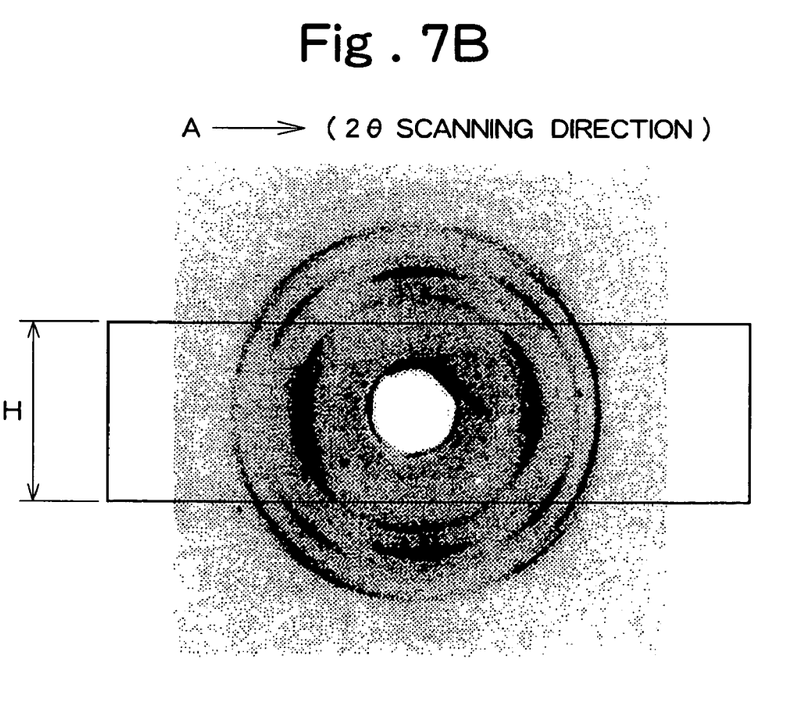

The debye rings shown in FIGS. 7A and 7B are obtained by measuring two samples having different crystalline orientations. FIG. 7A shows a case o crystal having low degree of preferred orientation, where crystals are arranged randomly. In this case, the Debye ring appears in a uniform ring shape. FIG. 7B shows a case of crystal having high degree of preferred orientation. In this case, the Debye ring appears in an arc, not a ring. When the degree of preferred orientation is increased further, dotted exposed portion appear on the Debye ring.

Figure 8A:
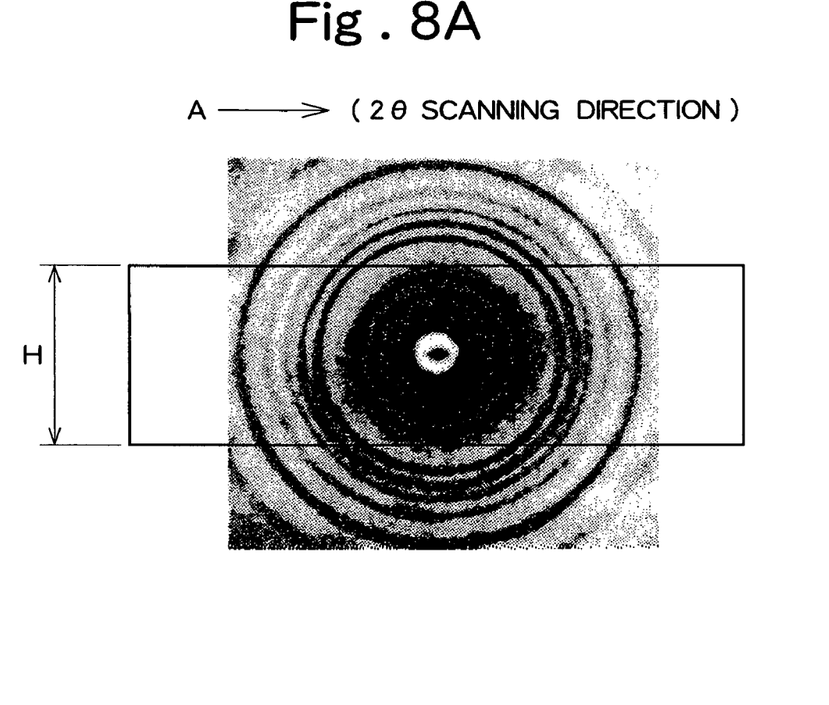
FIGS. 8A and 8B are views, each showing another example of the Debye ring obtained as a result of the measurement using the X-ray analysis apparatus.
Figure 8B:
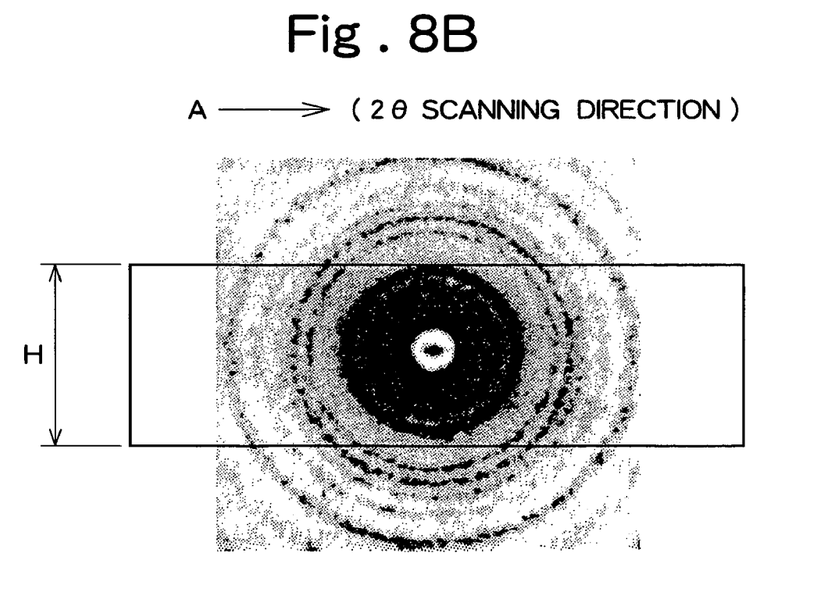

The Debye rings shown in FIGS. 8A and 8B are obtained by measuring two samples having different crystal diameters. FIG. 8A shows a case of small crystal diameter. In this case, the Debye ring appears clearly in line shape. FIG. 8B shows a case of large crystal diameter. In this case, the Debye ring appears in a dotted manner.

Referring to FIG. 1, information related to 2θ angular position of the 2θ-rotating CCD detector 11 is sent to the processing circuit 26 shown in FIG. 2 as the 2θ-signal output from the 2θ-rotating device 22. When the CCD detector 11 receives X-ray that constitutes a part of the Debye ring "Q", the X-ray intensity calculation circuit 16 calculates the height information and intensity information of the X-ray. The obtained information is output as the X-ray intensity signal I(h). Every time the 2θ data and I(h) data are sent from the 2θ-rotating device 22 and X-ray intensity calculation circuit 16, the CPU 27 shown in FIG. 2 stores the data into a predetermined file in the storage medium 31 and sends the same data to the graphic controller 37 of the image controller 32. That is, in the present embodiment, immediately after the CCD detector 11 has started to perform scanning operation, the 2θ data and I(h) data are introduced into the graphic controller 37. Every time the 2θ data and I(h) data are updated, the updated data items are introduced into the graphic controller 37.

As described above, in the present embodiment, the timings at which the X-ray intensity calculation circuit 16 performs the sampling of the X-ray intensity and 2θ angular positions are synchronized with each other by sending the 2θ signal output from the 2θ-rotating device 22 to the X-ray intensity calculation circuit 16 as the exterior trigger signal S2. Thus, if the output order of the X-ray intensity signal I(h) which is sequentially output from the X-ray intensity calculation circuit 16 can be identified, it is possible to know the 2θ angle from the order. Therefore, in the case where the X-ray intensity signal I(h) and angle 2θ are related to each other by this method, the CPU 27 does not store the 2θ data output from the 2θ-rotating device 22 into the storage medium 31 and send the 2θ data to the graphic controller 37, but computes the 2θ angle based on the output order of the I(h) data output from the X-ray intensity calculation circuit 16, store the computed 2θ angle data into the storage medium 31, and sends the same to the graphic controller 37.

On receiving the new 2θ data and I(h) data, the graphic controller 37 creates 1D, 2D, and 3D image data based on the received data. The created image data is synthesized on the video memory 38 into one frame image data that can be displayed in one screen. The synthesized image data is converted into an analog signal by the D/A converter 39 and displayed on the screen of the display unit 41.

Figure 3:
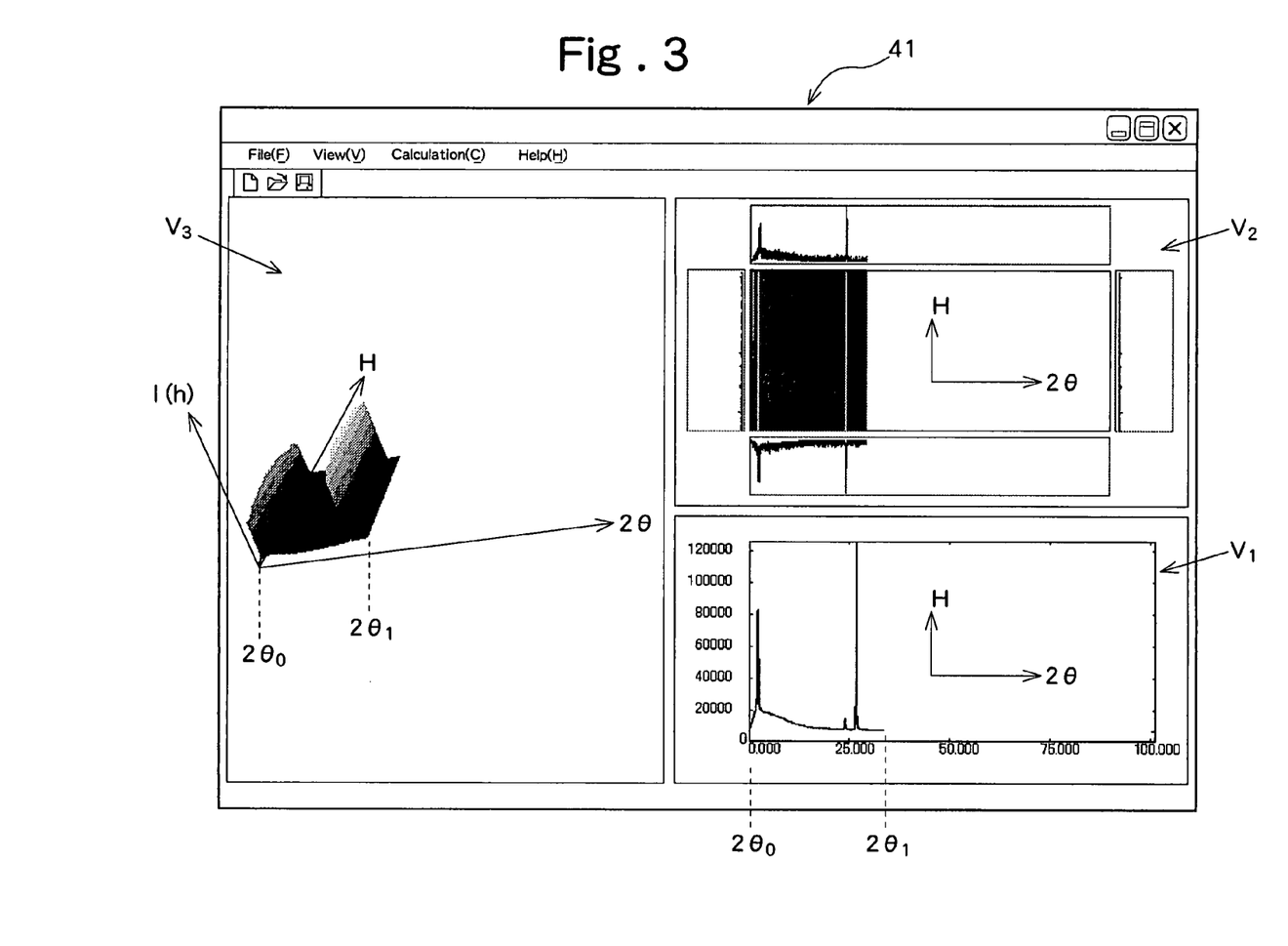
FIG. 3 is a view showing an example of the screen displayed on a display unit used in the electrical control system of FIG. 2.
Figure 4:
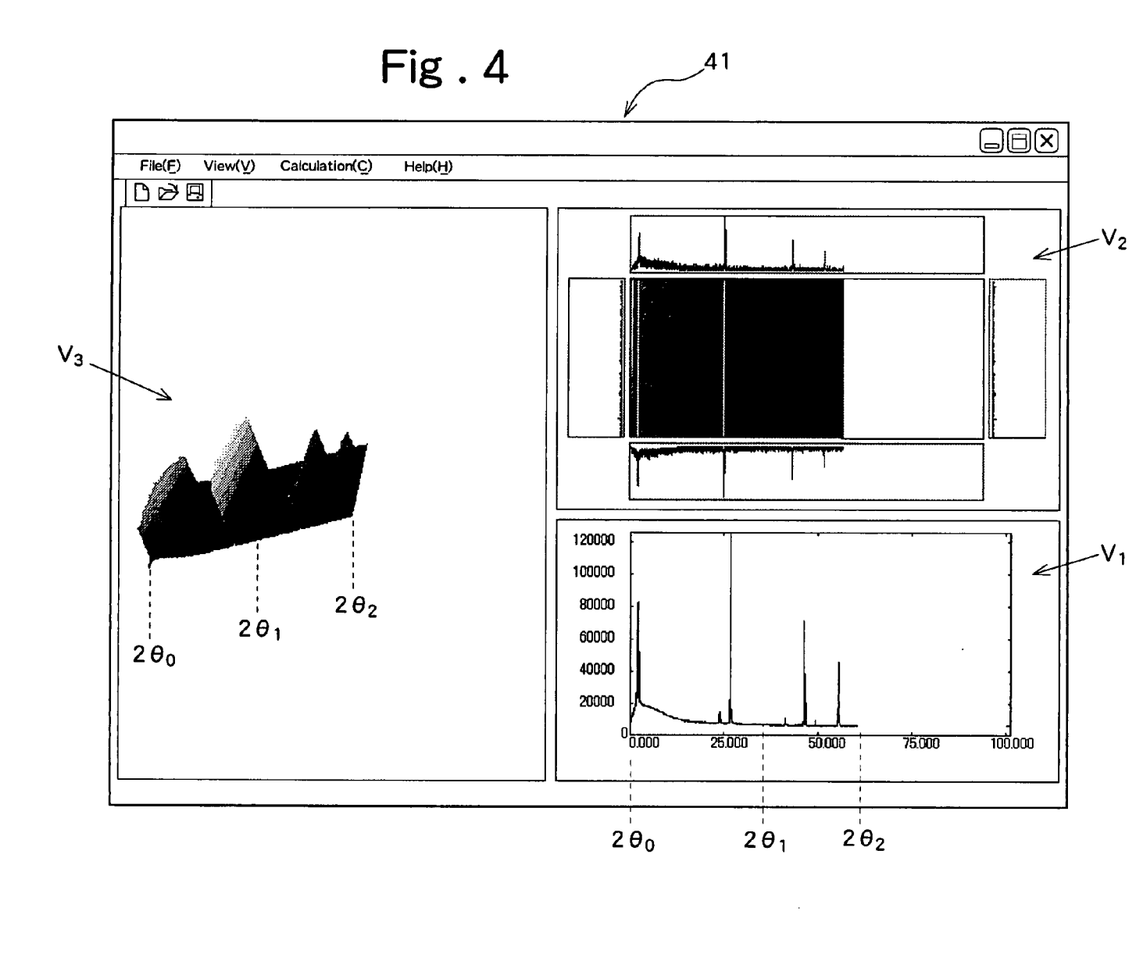
FIG. 4 is a view showing another example of the screen displayed on a display unit used in the electrical control system of FIG. 2.
Figure 5:
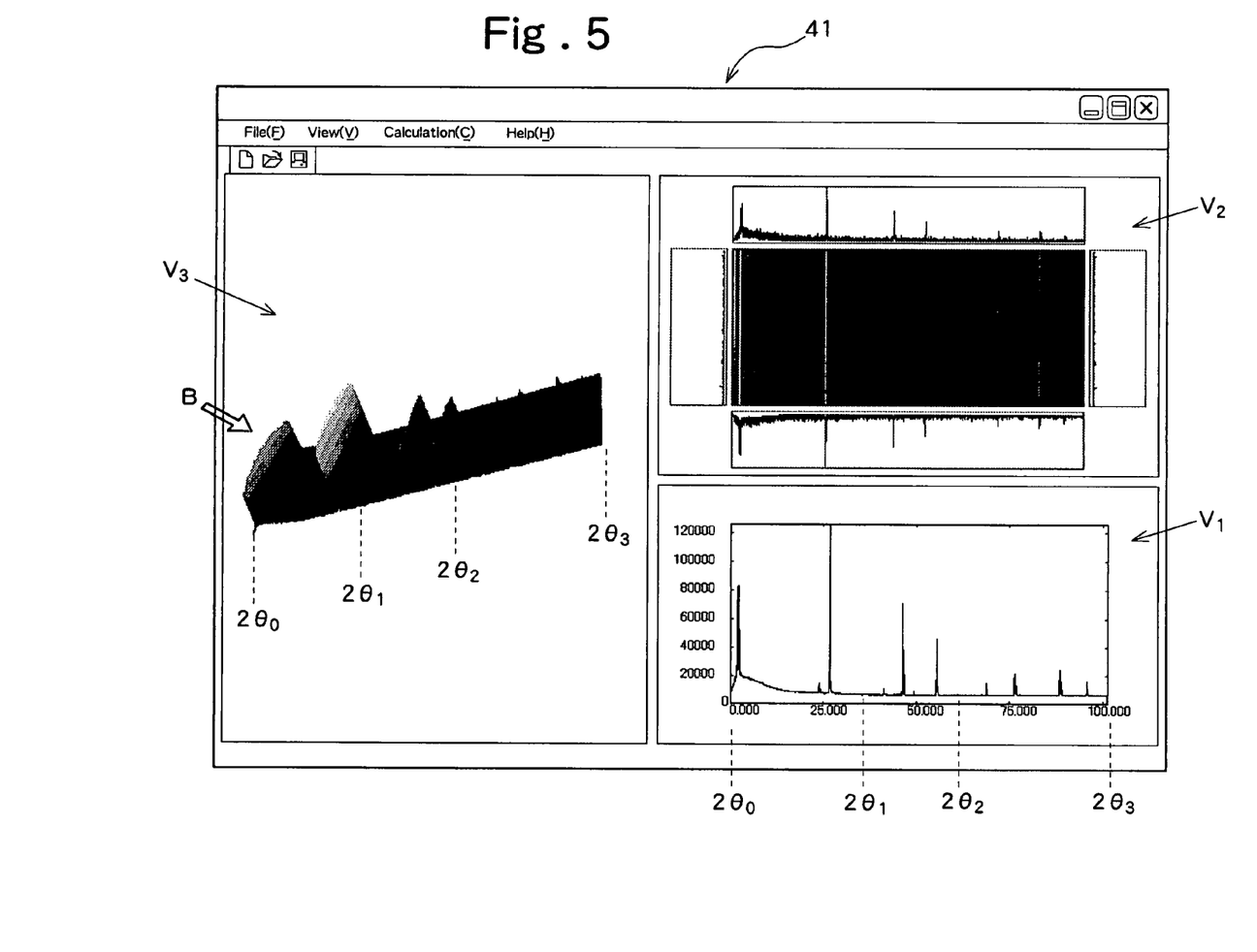
FIG. 5 is a view showing a still another example of the screen displayed on a display unit used in the electrical control system of FIG. 2.

FIGS. 3, 4, and 5 each show an example of a measurement result displayed on the screen as described above. In each of the drawings, an image V1 displayed in the lower right portion of the screen is the 1D image created based on the 1D image data, an image V2 displayed in the upper right portion of the screen is the 2D image created based on the 2D image data, and an image V3 displayed in the left portion of the screen is the 3D image created based on the 3D image data.

The 1D image V1 is a measurement result represented by a line obtained by plotting the 2θ data and I data on a coordinate system with the diffraction angle 2θ on the horizontal axis and the intensity "I" of X-ray on the vertical axis. The X-ray intensity "I" obtained at one 2θ angular position in the 1D image is the intensity obtained by integrating the X-rays that have been captured by the entire region or designated region in the height direction "H". A specific portion can be displayed in an enlarged or reduced size depending on the length of the scale set in the coordinate system.

The 2D image V2 is a bitmap-formatted pattern represented in a one-dimensional manner obtained by plotting the 2θ data and I(h) data on a coordinate system with the diffraction angle 2θ on the horizontal axis and the height direction "H" of the CCD detector 11 on the vertical axis. In this case, intensity change in the height direction "H" of the CCD detector 11 is represented as the difference in hue, or grayscale along the vertical axis. In the case of FIG. 3, high-intensity portions are represented as white, low-intensity portions are as black, and intermediate-intensity portions are as gray. The degree of the X-ray intensity in the intermediate portions can be identified by the shade of gray. That is, by observing the shade of gray in the height direction "H", it is possible to know the X-ray intensity distribution obtained at one 2θ angular position along the height direction "H". A specific portion can be displayed in an enlarged or reduced size depending on the length of the scale set in the coordinate system.

The 3D image V3 is a pattern represented in a three-dimensional manner, or perspective manner obtained by plotting the 2θ data and I(h) data on a 3-axis coordinate system with the diffraction angle 2θ on the horizontal axis, the height "H" of the CCD detector 11 on the depth axis, and the X-ray intensity I(h) on the vertical axis.

The 3D image data based on which the 3D image V3 is formed is created by the calculation of the 3D image processor in the graphic controller 37 of FIG. 2. As is well known, the 3D image processor performs a sequence of processes as follows to create the 3D image data: creating a 3D reference model by, for example, polygon mesh; converting the reference model into a relative coordinate which is based on the view point; generating color information in consideration of depth or direction of a light source; converting the 3D polygon coordinate system into a 2D coordinate system for 2D display; and actually plotting the 2D polygon onto a frame memory.

In the process of actually plotting the 2D polygon onto a frame memory, various image processing such as shading for screening out the unseen portions, texture mapping for pasting images onto the polygon, or mapping for pasting colors onto the polygon are performed. With the above 3D image processes, it is possible to view the 3D image V3 from different directions depending on the setting of a viewpoint.

The 3D pattern can be rotated, enlarged or reduced depending on the setting of coordinate positions of the polygon.

As described above, the graphic controller 37 creates 1D, 2D, and 3D image data based on the received data every time it receives the new 2θ data and I(h) data. Therefore, the X-ray intensity I(h) data corresponding to the region of the diffraction angle 2θ obtained as a result of the scanning operation of the CCD detector 11 is sequentially displayed on the display unit 41. That is, display of the 3D image V3 or the like is not performed after the scanning operation with respect to the entire region within the angular range targeted by the CCD detector 11 has been completed, but is started simultaneously with the scanning operation of the CCD detector 11.

Assume that an angular range of $2\theta_0$ to $2\theta_3$ is the desired measurement region, as shown in FIG. 5. The flow of the display in this case is not that a measurement result related to the entire angular range of $2\theta_0$ to $2\theta_3$ is displayed simultaneously at one time after the completion of the measurement, but that a measurement result related to the angular range of $2\theta_0$ to $2\theta_1$ is displayed firstly, a measurement result related to the angular range of $2\theta_0$ to $2\theta_2$ is then displayed, and, ultimately, a measurement result related to the angular range of $2\theta_0$ to $2\theta_3$ is displayed, as shown in FIGS. 3 and 4. That is, measurement results of the angular range from $2\theta_0$ to $2\theta_1$, that from $2\theta_0$ to $2\theta_2$, and that from $2\theta_0$ to $2\theta_3$ are sequentially displayed in a stepwise manner.

When the timings at which the display of the 3D image V3 or the like is started and ended correspond to a scanning starting angle 0° and a scanning end angle 100° of the CCD device 11 of FIG. 1, and a timing at which the display of the 3D image V3 or the like is updated corresponds to a scanning timing of the CCD detector 11, the measurement result is displayed on the display unit 41 in so-called "real time" during the scanning operation of the CCD detector 11. That is, every time the CCD detector 11 obtains new data through the scanning operation, the obtained data is sequentially displayed in a continuous fashion. The same applies to the case where the 1D or 2D image is displayed.

All the images V1, V2, and V3 or any combination among the images V1 to V3 may be displayed on the display unit 41 simultaneously with the scanning operation of the CCD detector 11.

In the case where the X-ray analysis is performed using the analyzer shown in FIG. 1, it may take several hours or several tens of hours, or in some cases, several days to end the measurement. Further, in a conventional X-ray analysis apparatus, an image corresponding to the 1D image V1 of FIG. 5 is displayed as the measurement result on the display unit simultaneously at one time after the completion of the measurement. Therefore, in the conventional X-ray analysis apparatus, the measurement result to be displayed on the display unit cannot be viewed until several hours or several tens of hours, or in some cases, several days have passed since completion of the measurement.

In another respect, there is a possibility that a sample used in the measurement does not have targeted crystal condition. Further, there is a possibility that a targeted measurement condition cannot be obtained. If the above cases occur in the measurement using the conventional X-ray analysis apparatus, an operator does not recognize the occurrence of theses cases until the measurement has been completed, that is, until the measurement result has been displayed after a long time has passed since completion of the measurement. The situation described above does nothing but waste time.

In the present embodiment, on the other hand, the measurement result starts being displayed in the middle of the measurement, as shown in FIGS. 3 and 4. Thus, if the sample itself or measurement condition is not in a normal state, the operator can become aware of the bad condition at an appropriate time point in the middle of the measurement without the need of waiting for completion of the measurement and can cope with the problem promptly, with the result that waste of time can be prevented. In addition, in the present embodiment, the 3D image V3 is displayed in the middle of the measurement. The 3D image V3 represents various kinds of information to the operator in a perspective manner, so that the operator can make an accurate determination promptly without making an error of judgment.

Further, in the present embodiment, all the images V1, V2, and V3 or any combination among the images V1 to V3 are displayed on one screen, as shown in FIG. 5. Accordingly, the operator can analyze the sample while comparing different images with each other. Therefore, it is possible to make a reliable determination in the shortest time. By displaying all the images V1, V2, and V3 simultaneously on one screen, the operator can make a highly reliable determination promptly.

Assume that only the 1D image V1 of FIG. 5 is displayed on the display unit. In this case, when the peak of the X-ray intensity occurs at a specific 2θ position, the operator can determine the physicality of the sample to some extent, but cannot make a fine determination such as whether crystalline orientation is high or low or whether the size of the crystal is large or small. In the present embodiment, on the other hand, the operator can observe the 2D image V2 or 3D image V3, or both of the two. Thus, the operator can accurately grasp the portion belonging to the range of the height "H" and scanning range of the CCD detector 11 in the Debye ring shown in FIGS. 7 and 8. Therefore, the operator can accurately grasp even the crystalline orientation or the state of the crystal grain in the sample.

Figure 6:
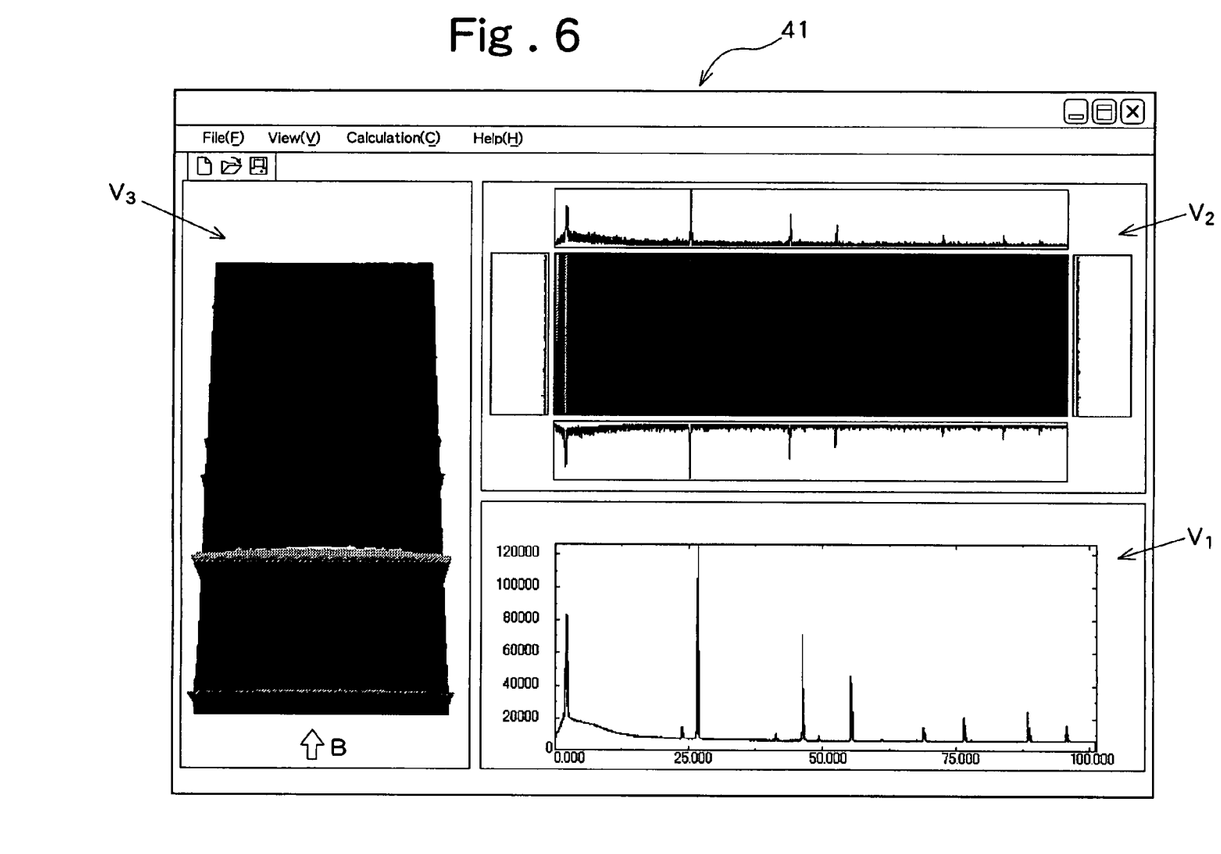
FIG. 6 is a view showing a still another example of the screen displayed on a display unit used in the electrical control system of FIG. 2.

To make a more accurate determination, it is effective to display the 3D image V3 from different directions, meaning different points of view, as shown in FIG. 6. The 3D image V3 shown in FIG. 6 is the image obtained by displaying the 3D image V3 of FIG. 5 from the view point "B".

ANOTHER EMBODIMENT

While the present invention has been described with reference to the preferred embodiment, it should be apparent that the present invention is not limited to the embodiment and may be embodied in many other specific forms without departing from the spirit or scope of the invention.

For example, the goniometer 3 having a configuration that allows the sample "S" to θ-rotate and the CCD detector 11 to 2θ-rotate at a speed double that of the θ-rotation in the embodiment shown in FIG. 1. Alternatively, another configuration may be adopted, in which the sample "S" is disposed in a fixed state, the X-ray generator 2 is allowed to θ-rotate in one direction, and the CCD detector 11 is allowed 2θ-rotate in the direction opposite to that of the X-ray generator 2 at the same angular speed.

Further, in the embodiment shown in FIG. 1, the CCD detector 11 is used as an X-ray detecting means having a linear X-ray capture region. Alternatively, a PSPC that is another type of one-dimensional detector may be used. Further, a two-dimensional X-ray detector including a plurality of CCDs arranged in a planar manner or another two-dimensional X-ray detector including a planer storage phosphor may be used. Then, a linear X-ray capture portion of the two-dimensional X-ray detector is used.

What is claimed is:

1. An X-ray analysis apparatus comprising:

X-ray radiation means for irradiating a sample with X-rays;

X-ray detecting means for detecting X-ray emission from the sample;

means for allowing the X-ray detecting means to perform scanning operation for changing the angle of the X-ray detecting means with respect to the sample; and image control means for displaying information related to X-ray intensity detected by the X-ray detecting means and information related to a scanning angle of the X-ray detecting means as a 3D image, wherein the image control means display a 3D image simultaneously with the scanning operation of the X-ray detecting means, the image control means starts displaying the 3D image before completion of scanning of the X-ray detecting means, the image control means gradually displays the 3D image in synchronization with the scanning operation of the X-ray detecting means.

2. The X-ray analysis apparatus according to claim 1, wherein the X-ray detecting means has an X-ray detection region extending in the direction perpendicular to that of the scanning operation.

3. The X-ray analysis apparatus according to claim 2, wherein the 3D image is displayed on a 3-axis coordinate system with a diffraction angle on the horizontal axis, X-ray detection region perpendicular to the scanning operation direction of the X-ray detecting means on the depth axis, and the X-ray intensity on the vertical axis.

4. The X-ray analysis apparatus according to claim 1, wherein the image control means sequentially displays the 3D image in synchronization with the scanning operation of the X-ray detecting means in a stepwise manner.

5. The X-ray analysis apparatus according to claim 1, wherein the image control means sequentially displays the 3D image in synchronization with the scanning operation of the X-ray detecting means in a continuous fashion.

6. The X-ray analysis apparatus according to claim 1, wherein the 3D image is gradually displayed in real-time in synchronization with the scanning operation.

7. An X-ray analysis apparatus comprising:

X-ray radiation means for irradiating a sample with X-rays;

X-ray detecting means for detecting X-ray emission from the sample;

means for allowing the X-ray detecting means to perform scanning operation for changing the angle of the X-ray detecting means with respect to the sample; and image control means for displaying information related to X-ray intensity detected by the X-ray detecting means and information related to a scanning angle of the X-ray detecting means simultaneously with the scanning operation of the X-ray detecting means using at least two image modes of 1D, 2D, and 3D images, the image control means starts displaying the information before completion of scanning of the X-ray detecting means;

the image control means gradually displays the information in synchronization with the scanning operation of the X-ray detecting means.

8. The X-ray analysis apparatus according to claim 7, wherein the X-ray detecting means has an X-ray detection region extending in the direction perpendicular to that of the scanning operation.

9. The X-ray analysis apparatus according to claim 7, wherein the 1D image is represented, by a line, on a coordinate system with a diffraction angle on the horizontal axis and the X-ray intensity on the vertical axis, the 2D image is represented, in a one-dimensional manner, on a coordinate system with the diffraction angle on the horizontal axis and X-ray detection region perpendicular to the scanning operation direction of the X-ray detecting means on the vertical axis, and the 3D image is represented, in a perspective manner, on a 3-axis coordinate system with the diffraction angle on the horizontal axis, X-ray detection region perpendicular to the scanning operation direction of the X-ray detecting means on the depth axis, and the X-ray intensity on the vertical axis.

10. The X-ray analysis apparatus according to claim 7, wherein the image control means sequentially displays all the 1D, 2D and 3D images or any combination among the three in synchronization with the scanning operation of the X-ray detecting means in a stepwise manner.

11. The X-ray analysis apparatus according to claim 7, wherein the image control means sequentially displays all the 1D, 2D and 3D images or any combination among the three in synchronization with the scanning operation of the X-ray detecting means in a continuous fashion.

12. The X-ray analysis apparatus according to claim 7, wherein the image modes are gradually displayed in real-time in synchronization with the scanning operation.

* * * * *